United States Patent [19]

Katopodis

[11] Patent Number: 5,296,346

[45] Date of Patent: Mar. 22, 1994

[54] METHOD FOR DETERMINING LIPID BOUND SIALIC ACID IN PLASMA

[76] Inventor: Nonda Katopodis, 10 Greens Cir., Stamford, Conn. 06903

[21] Appl. No.: 615,597

[22] Filed: Nov. 19, 1990

[51] Int. Cl.$^5$ .................. G01N 33/48; C12Q 1/00
[52] U.S. Cl. .......................................... 435/4; 435/18; 435/2; 436/63; 436/64; 436/71; 436/87; 436/93; 436/129; 436/178; 436/813
[58] Field of Search ............... 436/64, 63, 94, 87, 436/71, 177, 178, 129, 813, 93, 164; 530/420; 435/4, 18

[56] References Cited

U.S. PATENT DOCUMENTS

| | | | |
|---|---|---|---|
| 4,701,418 | 10/1987 | Katopodis | 436/64 |
| 4,748,128 | 5/1988 | Katopodis | 436/64 |
| 4,837,144 | 6/1989 | Sugiyama | 436/64 |
| 5,045,453 | 9/1991 | Katopodis | 436/64 |

*Primary Examiner*—James C. Housel
*Assistant Examiner*—David Redding
*Attorney, Agent, or Firm*—Paul L. Bollo

[57] ABSTRACT

The amount of lipid bound sialic acid in a blood plasma or serum sample may be determined by an improved method which may be automated involving the following steps to be performed simultaneously on the sample and a known standard prepared from human or animal blood or tissue; diluting with distilled water; mixing; adding a mixture of a chlorinated lower aklyl alcohol; mixing, diluting with water and then treating by mixing further and centrifuging to yield a substantially clear upper phase; recovering the upper phase and adding to it a protein precipitating agent, mixing the resulting admixture; recovering the resulting precipitate, suspending the precipitate in a hydrolysis agent and determining the amount of lipid bound sialic acid present by comparing the optical density of the sample to the optical density of the standard.

23 Claims, No Drawings

METHOD FOR DETERMINING LIPID BOUND SIALIC ACID IN PLASMA

BACKGROUND OF THE INVENTION

This invention concerns an improved method for the determination of lipid bound sialic acid in plasma or serum which is less expensive, less time consuming, less variable from sample to sample, and less dependent upon the skill and experience of the person performing the test. Additionally this invention concerns an improved test kit which contains a unique standard which will allow greater reproducibility of test results and more consistency throughout the world.

Much work has been done which indicates that elevated sialic acid content in blood sera of a patient is an indication of the presence of cancer. For example, U.S. Pat. No. 4,146,603 to Davidson, et al. discloses and claims a fairly complex series of procedures whereby elevated sialic acid content is a determinant with respect to cancer specific determinations.

MacBeth and Bekesi, Cancer Res. 22:1170–1176 (1962) measured plasma glycoproteins and found galactose and mannose values were seen in breast cases without metastases. Kloppel, et al., Proc. Natl. Acad. Sc. 74:3011–3013 (1977) reported 2.5-fold increases of serum sialic acid glycolipids in mice bearing transplantable mammory carcinomas and 2-fold increases in human carcinoma patients. Kloppel, et al., Am. J. Vet. Res. 39:1377–1380 (1978) also reported increases of sialic acid in 93% of 24 dogs; In leukemia AKR/J mice, Lengle, J. Natl. Cancer Inst. 62:1565–1567 (1979) found increased lipid bound sialic acid in their plasma and thymic lymphocytes. Lipid bound sialic acid levels were found increased in plasma and erythrocytes of humans bearing melanomas, Portouklian, et al., Biochem. Biophys. Res. Commun. 85:916–920 (1978). Chromatographic separation and purification on columns was followed by evaluation on chromatoplates. Silver, et al., Cancer 41:1497–1499 (1978); Cancer Res. 39:5036–5042 (1979) have reported elevated serum sialic acid values in melanoma patients that were significantly related to the tumor burden. However, 36% of patients with observable tumors showed no elevated serum sialic acid. Hogan-Ryan, et al., Br. J. Cancer 41:587–592 (1980) reporting on total bound serum sialic acid in patients with breast cancer found elevations that corresponded with tumor stage.

One specific method over which the present invention is an improvement is disclosed in the American Association for Cancer Research Annual Meeting PROCEEDINGS Vol 21, March 1980 as Abstract No. 728 by Katopodis, et al. Briefly, this method requires that a 100 ul plasma sample (reduced to 50 ul) be extracted with 6 ml of a chloroform/methanol mixture, (2 to 1, volume to volume ratio). The lipid extract is then partitioned with 0.2 of its volume of water. The aqueous phase is evaporated to dryness and the residue redissolved in water. The lipid bound sialic acid is then purified by trichloroacetic acid-phosphotungistic acid precipitation and, after the removal of the supernatant from the resultant precipitate, the precipitate is determined by the Svennerholm and Miettien method (Svennerholm, Quantitative Estimation of Sialic Acid...,Biochem. Biophys, Acta. 24, pp. 604–611 (1957)).

Another specific method over which the present invention is an improvement is disclosed in Katopodis and Stock, U.S. Pat. No. 4,342,567, issued Aug. 3, 1982. This method is similar to the foregoing but requires only about 50 ul of sample rather than the 100 ml required by the prior art method. The drying step is eliminated and there is no use of trichloracetic acid. Phosphotungstic acid is used alone.

These specific methods suffer from a number of disadvantages including the following: the need for a precisely defined 44.7 ul starting sample; lipid bound sialic acid is lost during the tube inversion step creating reduced final values; precipitation of the lipid bound sialic acid with phosphotungstic acid is not complete, which is a particular problem when working with samples in which the amount exceeds normal values by only small amounts (e.g. early in cancer development); the rapidity of the test is limited by the 5 minutes waiting time after phosphotungstic acid addition and the cost of the test is not as low as is desirable. Another method over which the present invention is an improvement is disclosed in U.S. Pat. No. 4,748,128, issued May 31, 1988 (Katopodis). This prior method consists of the following steps:

(a) diluting a predetermined volume of a blood plasma or serum with distilled water to a volume about four times that of the predetermined volume;

(b) mixing the diluted sample for a suitable period of time to obtain a substantially homogeneous sample;

(c) cooling the mixed, diluted sample to about 0 degrees to 5 degrees C.;

(d) adding to the cooled sample a mixture of a chlorinated lower alkyl hydrocarbon and a lower alkyl alcohol, the volume of the mixture added being about sixty times the predetermined volume of the blood plasma or serum sample, and the volume ratio of chlorinated hydrocarbon to alcohol in the mixture being about 2:1 and its temperature about 0 degrees to 5 degrees C.;

(e) mixing the resulting admixture for a suitable period of time to dissolve matter present in the sample in the chlorinated hydrocarbon/alcohol mixture;

(f) diluting the admixture with deionized distilled water at a temperature from about 0 degrees to 5 degrees C., the volume added being about ten times the predetermined volume of the blood plasma or serum sample;

(g) treating the diluted admixture for a suitable period of time to permit formation of a substantially clear upper phase;

(h) separately recovering from the clear upper phase so formed a predetermined volume of the upper phase;

(i) adding to the predetermined volume of the upper phase an amount of a mixture of a protein-precipitating agent and an adsorbing material, the amount of mixture being effective to cause precipitation of the lipid bound sialic acid and to adsorb the precipitated lipid bound sialic acid;

(j) mixing the resulting admixture;

(k) separately recovering the resulting adsorbed precipitate;

(l) suspending the precipitate in a suitable volume distilled water; and (m) adding to the suspended precipitate a volume of resorcinol reagent, mixing, boiling for 15 minutes, cooling for 10 minutes in an ice bath, centrifuging, adding a mixture of butylacetates and n-butanol (85:15 v/v) in a volume about twice the volume of the resorcinol reagent mixing, centrifuging, separating the organic layer, reading at 580 nm the extracted blue color present in the organic layer, and determining the amount of lipid bound sialic acid by comparing the optical density reading obtained at 580 nm to a standard curve developed from a known sample of n-acetyl neuraminic acid (NANA) under the same conditions and applying the formula:

$$LSA\ (mg/100\ ml\ plasma) = (x\ 10\ ul)/y\ z\ ul\ 1000)$$

where x=NANA read from the standard curve, y=the volume of the upper phase recovered divided by the total volume of the entire upper phase and z =the predetermined volume of the blood plasma or serum sample.

The present invention provides an improved method for determining the amount of lipid bound sialic acid present in a sample of plasma or serum. The present invention is more economical, more time efficient, more easily automated, and requires less labor and chemical reagents than the methods of the prior art. The procedure of the present invention differs significantly from known methods in that the present invention requires a much smaller sample of blood plasma or serum, eliminates the need to cool the mixture to a point below room temperature, and eliminates the need to use an adsorbing material. Moreover the present invention uses an unique standard which provides greater uniformity and better reproducibility from laboratory to laboratory and which enables the user to more easily and more accurately determine the level of sialic acid in the sample.

The present invention requires a plasma or serum sample of only about one-half of that required by the prior art. The ability to use a smaller sample has important advantages. It facilitates obtaining a sample from children and elderly patients as only a prick of the finger is required rather than the drawing of blood from a vein. It allows many more tests to be conducted from a volume of blood plasma or serum. For example the present invention permits twice as many tests of 50 ul of a sample of plasma or serum than the procedure of U.S. Pat. NO. 4,748,128 (Katopodis). The ability to conduct the test on smaller samples is also important in the screening and testing of new drugs on mice and rats. For example, use of the smaller samples of the invention allows a mouse to be bled each day without disturbing its metabolism. This permits more accurate testing since the effect of a drug on a single mouse can be tracked rather than requiring the test to be conducted on many mice and then averaged.

The prior art requires facilities to cool the mixture to zero degrees centigrade or below and requires the use of an adsorbing material made of siliceous material usually silica or silica gel. The present invention does not require ice making equipment which is expensive and not available in many laboratories around the world.

Significantly the present invention provides an improved procedure for determining the concentration of lipid bound sialic acid in a sample of human blood plasma or serum by comparing the sample with a known standard comprised of a similar substance, i.e. human or animal blood plasma or serum rather than a chemical, i.e. n-acetyl neuraminic acid (NANA) as in the prior art. It also eliminates the need to construct a standard curve for the standard as in the prior art. The improved procedure also eliminates the deviation between the optical density found for the sample and the standard curve due to variations in the techniques employed in carrying out the test procedure.

SUMMARY OF THE INVENTION

The present invention provides a method for extracting sialic acid from a sample of human blood plasma or serum and determining the amount of lipid bound sialic acid present in the sample which includes the following steps:

(a) diluting a predetermined volume of a blood plasma or serum sample with distilled water to a volume about two times that of the predetermined volume;

(b) mixing the diluted sample for a suitable period of time to obtain a substantially homogenous sample;

(c) adding to the sample a mixture of a chlorinated lower alkyl hydrocarbon and a lower alkyl alcohol, the volume of the mixture added being about forty times the predetermined volume of the blood plasma or serum sample, and the volume ratio of chlorinated hydrocarbon to alcohol in the mixture being about 2:1;

(d) mixing the resulting admixture for a suitable period of time to dissolve lipid bound sialic acid present in the sample in the chlorinated hydrocarbon/alcohol mixture;

(e) diluting the admixture with buffer solution, the volume being added about eight times the predetermined volume of the blood plasma or serum sample;

(f) treating the diluted admixture for a suitable period of time to permit formation of a substantially clear upper phase;

(g) separately recovering from the clear upper phase so formed a predetermined volume of the upper phase;

(h) adding to the predetermined volume of the upper phase an amount of a mixture of a protein-precipitating agent, the amount of mixture being effective to cause precipitation of the lipid bound sialic acid;

(i) mixing the resulting admixture;

(j) separately recovering the resulting precipitate;

(k) suspending the precipitate in a hydrolysis agent; and (l) determining the amount of lipid bound sialic acid present in the suspended precipitate and thereby the amount present in the blood plasma or serum sample.

The determination of the amount of lipid bound sialic acid in the sample is made by comparing the optical density of the sample to that of a known standard derived from human tissue, human blood or animal blood. Animal blood is preferred because it is readily available and normally free from contamination causing infectious disease to humans.

The standard is prepared using the following steps:

(a) extracting the blood plasma or serum from the whole blood;

(b) diluting a predetermined volume of the plasma or serum sample with an equal volume of distilled water;

(c) mixing the diluted sample for a suitable period of time to obtain a homogenous sample;

(d) adding to the sample a lower alkyl alcohol, the values of the alcohol added being about five times the predetermined value of the sample;

(e) mixing the resulting admixture for a suitable period of time to dissolve matter present in the sample in the alcohol mixture;

(f) treating the admixture for a suitable period of time to permit the formation of a supernatant and a precipitate;

(g) diluting the precipitate with distilled water which solution is the standard to be used in the test;

(h) determining the amount of lipid bound sialic acid present in the standard by use of a standard curve developed for n-acetyl neuraminic acid (NANA).

A volume of the standard equivalent to the volume of the sample being tested is treated exactly the same as, and simultaneously with, the sample according to the procedure set forth above for the sample.

The concentrate of lipid bound sialic acid in the sample is found by multiplying the optical density of the sample times the known concentration of lipid bound sialic acid of the standard and dividing the product by the optical density of the standard.

The improved procedure of the invention provides improved reproducibility of the test and improved accuracy of the test results in any laboratory because the test sample and the known standard are treated with exactly the same techniques. Thus variations between the test results for the sample and a standard which are due to variations in the procedures or techniques used in testing the sample are eliminated.

This invention also provides a method and kit for diagnosing cancer in a human subject which comprises determining the amount of lipid bound sialic acid in a sample of a subject's blood plasma or serum and comparing the amount obtained with values obtained for subjects known to have cancer.

Alternatively the method and kit of this invention may be used to regularly determine the amount of lipid bound sialic acid present in a subject's blood plasma or serum and thus to monitor the progress of therapy of a subject by comparing each amount so determined with amounts previously determined for the subject.

Another aspect of the invention concerns a method of diagnosing cancer in a human subject which comprises determining the amount of lipid bound sialic acid in a sample of the subject's plasma or serum according to the method of the present invention and comparing the amounts so determined with values obtained for subjects known to have cancer, or alternatively, comparing the amount so determined with values obtained over a period of time for the same subject.

The invention also provides a method for monitoring the progression of cancer in a subject which comprises determining at regular time intervals the amount of lipid bound sialic acid in a sample of the subject's blood plasma or serum according to the method of the present invention and comparing the amount so determined with amounts previously obtained for the subject.

Furthermore, this invention provides an improved cancer diagnostic kit comprising a container with a mixture of a lower alkyl alcohol and chlorinated lower alkyl hydro-carbon; a container of prediluted resorcinol reagent; a container with a stabilizer buffer solution and a mixture of butyl acetate and n-butanol (85:15 volume ratio); a container of a standard in powder form having a known concentration of lipid bound sialic acid; and instructions enabling the user of the kit to conduct the test and compare it to the standard provided to determine the amount of lipid bound sialic acid in the sample without variations between the sample and the standard resulting from the techniques or procedures used by the person conducting the test.

DETAILED DESCRIPTION OF THE INVENTION

The amount of lipid bound sialic acid in a sample of human blood plasma or serum may be determined and the amount so determined used as a diagnostic indicator of cancer. A preliminary step to the method is to obtain a sample to be tested. The sample will typically be recovered from whole blood drawn from a subject and treated using methods which are well known and described in the prior art. See, for example, Katopodis, U.S. Pat. No. 4,748,128.

The initial step of the method of the present invention is to dilute a predetermined volume of a blood plasma or serum sample with buffer solution. The volume dilution is about two times the volume of initial plasma sample. Thus, if the initial plasma or serum sample is 25 ul in a small tube or container, the amount of distilled water added may be about 50 ul to produce about 75 ul of diluted sample, i.e., about three times the volume of the initial sample.

The diluted sample is mixed, e.g., by vortexing, for a suitable time to obtain a substantially homogeneous sample, e.g., at least 5 seconds.

The present invention eliminates the need for cooling to 0° C. as required in the prior art thus enabling many laboratories in third world nations which do not have ice making equipment to use this invention.

A mixture of a chlorinated lower alkyl hydrocarbon and a lower alkyl alcohol in which the volume ratio of chlorinated hydrocarbon to alcohol is about 2 to 1 is then added to the sample. The volume of the chlorinated hydrocarbon and alcohol mixture added is about forty times the original, i.e., predetermined, volume of the plasma sample and its temperature is room temperature. Thus, if the original sample volume is 25 ul, then the volume of mixture added is about 1.0 ml. Suitable chlorinated hydrocarbons include chloroform, methylene chloride and ethylene chloride, chloroform being presently preferred. The lower alkyl alcohol may be methanol, ethanol, propanol, n-butanol, isopropanol, isobutanol or isoamyl alcohol. The greater the number of carbon atoms in the alcohol, the less effective the mixture is in terms of lipid bound sialic acid extraction as opposed to total sialic acid extraction. Therefore, the preferred alcohol is methanol since the other alcohols extract higher amounts of total sialic acid and other contaminants, and therefore reduce the diagnostic value of the test.

The resulting admixture is then mixed for a suitable period of time to dissolve lipid bound sialic acid present in the sample in the chlorinated hydrocarbon/alcohol mixture, by gentle inversion. Mixing by vortexing, as in the prior art, produces an emulsion which is very difficult to separate. The admixture is then diluted with buffer, at room temperature, the volume added being about eight times the predetermined volume of the blood plasma or serum sample. Thus, if the original plasma sample were 25 ul and the amount of chlorinated hydrocarbon:alcohol mixture was 1.0 ml, the amount of water added would be about 0.2 ml.

The diluted admixture is then treated, first by mixing the diluted admixture for a suitable period of time, e.g., by gentle inversion for at least 30 seconds. Vortexing as in the prior art may adversely affect the test results. The mixture is then centrifuged for at least about five minutes at about 3500 rpm to yield a substantially clear upper phase.

A predetermined volume of the upper phase is then separately recovered from the substantially clear upper phase so formed, preferably by removing the upper phase from the lower phase and discarding the latter. The predetermined volume so recovered will depend upon the volume of the original plasma sample. Thus, if the original, i.e. predetermined, plasma volume is about 25 ul, the volume of upper phase separately recovered will be about 0.2 ml. The predetermined volume of the upper phase which is separately recovered will depend upon the convenience of removing a large volume of the upper phase without disturbing the interface or other material in the tube.

To the predetermined volume of the upper phase there is added an amount of a protein-precipitating agent, the amount added being effective to cause precipitation of the lipid bound sialic acid. Suitable protein-precipitating agents include phosphotungstic acid, trichloroacetic acid, ammonium sulfate or mixtures thereof (e.g., 90% phosphotungistic acid; 10% trichloracetic acid), preferably a phosphotungstic acid solution with water (1:3 wt/vol). The invention eliminates the need for the addition of adsorbing materials such as silica and silica gel as required by the prior art.

The resulting admixture is then mixed, e.g., by vortexing briefly (at least 3 seconds), and the resulting precipitate is recovered, e.g., by centrifugation for at least 3 minutes at a speed above 1500 rpm, and discarding the supernatant. The precipitate is then suspended in a suitable volume of resorcinal agent e.g., 0.5 ml, then treated by mixing, boiling for 15 minutes, cooling for at least about 5 minutes, adding about twice said suitable volume, e.g., 1 ml, of a mixture of butyl acetate and n-butanol (85:15 v/v), mixing, centrifuging for at least 5 minutes at above about 2500 rpm, separating the organic layer, reading at 580 nm the extracted blue color present in the organic layer, determining the amount of lipid bound sialic acid using the optical density of a known standard which is treated exactly the same as the sample, and simultaneously therewith, and applying the formula:

$$\text{LSA (mg/100 ml plasma)} = \frac{A \times B}{C}$$

Where A=the known concentration of lipid bound sialic acid in the standard; B=the optical density of sample; and C=the optical density of the standard.

Another important aspect of the present invention is the method for preparing the standard used in the foregoing procedure. The standard may be human blood plasma or serum, animal blood plasma or serum, or an extract from animal or human tissue. Animal blood plasma or serum is preferred because animal blood is inexpensive, is readily available in large quantities and is normally free of bacterial or viral contaminations. The plasma or serum is obtained by centrifuging the whole animal blood at 2500 rpm for 10 minutes at room temperature. 100 ml of serum or plasma is extracted in the normal manner well known in the prior art. 100 ml of either the plasma or serum is used to prepare the standard. 100 ml of plasma or serum is transferred to a large container and mixed with an equal volume of distilled water. The mixture is mixed vigorously for about 5 minutes. To this mixture is added 500 ml of alcohol, preferably methanol, and the mixture is vigorously mixed for an additional 5 minutes. The mixture is then transferred to centrifuge tubes and centrifuged at 2500 rpm for 10 minutes at room temperature. The supernatant is transferred to a flask for further treatment as described below. The precipitate is suspended in 100 ml of distilled water. This solution is the standard. Each 1 ml of the standard is transferred to a separate vial and lyophilyzed to a dry powder by procedures well known in the art. 1 ml of a buffer solution is used to reconstitute the standard for analysis. The concentration of lipid bound sialic acid in the standard is determined by use of a standard curve developed from a standard sample of n-acetyl neuraminic acid (NANA). It should be understood that the collected supernatant may also be used for the preparation of the standard. This is done by condensing the supernatant to 1/10 of its volume by rotary evaporation. This volume of the supernatant is then purified by extraction with a chloroform-methanol mixture and partitioned with water.

The improved reliability, accuracy and reproducibility of the present invention can be seen from the following tables. In Table I, showing the results of tests on the blood of normal subjects, the standard deviation of the results using the method of the prior art (U.S. Pat. No. 4,748,128 (Katopodis) is 2.45 while the standard deviation of the results of tests using the method of the present invention is 0.87. In Table II, showing the test results on the blood of patients having cancer, the standard deviation of test results using the method of the prior art is 6.31 while the standard deviation using the method of the present invention is 2.79.

TABLE I

Percent of Lipid Bound Sialic Acid in healthy patients (mgs per 100 ml)

| Present Invention | | Prior Art |
|---|---|---|
| 21.0 | | 23.4 |
| 21.3 | | 23.7 |
| 22.0 | | 24.4 |
| 19.7 | | 22.1 |
| 19.7 | | 22.1 |
| 20.8 | | 18.4 |
| 22.0 | | 19.6 |
| 19.0 | | 16.6 |
| 21.0 | | 23.4 |
| 21.0 | | 18.6 |
| 19.3 | | 18.6 |
| 19.9 | | 21.7 |
| 21.0 | | 18.6 |
| 21.0 | | 23.4 |
| 20.0 | | 22.4 |
| 19.4 | | 17.0 |
| 19.6 | | 22.0 |
| 21.3 | | 23.7 |
| 21.0 | | 23.4 |
| 20.5 | mean | 21.28 |
| 0.870 | standard deviation | 2.45 |

TABLE II

Percent of Lipid Bound Sialic Acid in Cancer Patients (mgs per 100 ml)

| Present Invention | Prior Art |
|---|---|
| 45.3 | 41.4 |
| 48.4 | 44.5 |
| 52.1 | 56.0 |
| 50.8 | 54.7 |
| 49.8 | 45.9 |
| 44.4 | 40.5 |
| 51.2 | 55.1 |
| 50.6 | 54.5 |
| 50.4 | 54.3 |
| 48.6 | 44.7 |
| 49.9 | 46.0 |
| 52 | 55.9 |
| 54.1 | 58.0 |
| 50.5 | 54.4 |
| 56.3 | 60.2 |
| 46.8 | 42.9 |
| 49.4 | 45.5 |
| 53.3 | 57.2 |
| 48 | 44.1 |
| 48 | 44.1 |

TABLE II-continued

| Percent of Lipid Bound Sialic Acid in Cancer Patients (mgs per 100 ml) | | |
|---|---|---|
| Present Invention | | Prior Art |
| 49.99 | mean | 49.99 |
| 2.79 | standard deviation | 6.31 |

What is claimed is:

1. A method of extracting lipid bound sialic acid from human blood plasma or serum and determining the amount of lipid bound sialic acid in a sample of human blood plasma or serum which comprises the following steps:
   a) diluting a predetermined volume of 25 microliters or less of a blood plasma or serum sample with distilled water to a volume about two times that of the predetermined volume of the sample;
   b) mixing the diluted sample for a suitable period of time to obtain a substantially homogeneous sample;
   c) adding to the sample a mixture of a chlorinated lower alkyl hydrocarbon and a lower alkyl alcohol, the volume of the mixture added being about forth times the predetermined volume of the blood plasma or serum sample, and the volume ratio of chlorinated hydrocarbon to alcohol in the mixture being about 2:1;
   d) mixing the resulting admixture for a suitable period of time to dissolve lipid-bound sialic acid in the sample in the chlorinated hydrocarbon/alcohol mixture;
   e) diluting the admixture with a buffer solution at room temperature, the volume of buffer solution being about eight times the predetermined volume of the blood plasma or serum sample;
   f) mixing the diluted admixture without vortexing for a suitable period of time to obtain a substantially homogeneous admixture and centrifuging the mixture to form a substantially clear upper phase;
   g) separately recovering from the clear upper phase so formed a predetermined volume of the upper phase;
   h) adding to the predetermined volume of the upper phase an amount of a mixture of a protein-precipitating agent and water without any adsorbing material, the amount of mixture being effective to cause precipitation of the lipid bound sialic acid;
   i) mixing the resulting admixture;
   j) separately recovering the resulting precipitate;
   k) suspending the precipitate in a hydrolysis agent;
   l) determining the amount of lipid bound sialic acid present in the suspended precipitate and thereby the amount present in the blood plasma or serum sample.

2. A method according to claim 1, wherein in step (b) the mixing takes place for at least 2 seconds.

3. A method according to claim 1, wherein in step (c) the volume of the added mixture is about 1 ml.

4. A method according to claim 1, wherein in step (c) the lower alkyl alcohol is methanol, ethanol, propanol, n-butanol, isopropanol, isobutanol or isoamyl alcohol.

5. A method according to claim 4, wherein in step (c) the lower alkyl alcohol is methanol.

6. A method according to claim 1, wherein in step (c) the chlorinated lower alkyl hydrocarbon is chloroform.

7. A method according to claim 1, wherein in step (d) the mixing takes place for at least 10 seconds.

8. A method according to claim 1, wherein in step (a) the volume of water added is about 0.2 ml.

9. A method according to claim 1, wherein in step (f) the mixing comprises gentle inversion for at least 30 seconds followed by centrifuging at above 3500 rpm for at least 5 minutes.

10. A method according to claim 1, wherein in step (g) the separately recovering comprises removing the upper phase from the lower phase.

11. A method according to claim 1, wherein in step (g) the predetermined amount of the upper phase is about 0.2 ml.

12. A method according to claim 1, wherein in step (h) the protein-precipitating agent is phosphotungstic aoid, trichloroacetic acid, ammonium sulfate or a mixture thereof.

13. A method according to claim 1, wherein in step (h) the mixture comprises 25 ml of phosphotungstic acid and distilled water in a volume ratio of 1:3.

14. A method according to claim 1, wherein in step (i) the mixing takes place for at least 3 seconds.

15. A method according to claim 1, wherein in step (j) the separately recovering comprises centrifuging for at least 3 minutes at a speed above about 1500 rpm.

16. A method according to claim 11, wherein in step (k) the hydrolysis agent is resorcinol.

17. A method according to claim wherein step (l) the amount of lipid bound sialic acid is determined by adding to the suspended precipitate a volume of resorcinol reagent, mixing, boiling for 15 minutes, cooling for about 5 minutes in cold water, adding a mixture of butylacetate and n-butanol (85:15 v/v) in a volume about twice said volume of resorcinol reagent mixing, centrifuging for about 5 minutes at above 2500 rpm, separating the organic layer, reading at 580 nm the extracted blue color present in the organic layer, determining the amount of lipid bound sialic acid by comparing the reading obtained at 580 nm to that obtained for a standard having a known amount of lipid bound sialic acid and applying the formula:

$$\text{LSA (mg/100 ml plasma)} = \frac{A \times B}{C}$$

Where A = the concentration of the standard, B = the optical density of the sample and C = the optical density of the standard.

18. A method according to claim 17, wherein the known standard is tested exactly the same as, and simultaneously with, the sample in accord with the method of claim 1.

19. A method according to claim 18, wherein the standard is animal blood plasma or serum, human blood plasma or serum or an extract of human or animal tissue.

20. A method according to claim 17, wherein the volume of resorcinol reagent is about 0.5 ml.

21. A method of diagnosing cancer in a human subject which comprises determining the amount of lipid bound sialic acid in a sample of the subject's blood plasma or serum according to the method of claim 1 and comparing the amount so determined with values obtained for subjects known to have cancer.

22. A method of diagnosing cancer in a human subject which comprises determining at regular time intervals the amount of lipid bound sialic acid in a sample of the subject's blood plasma or serum according to the method of claim 1 and comparing the amounts so determined with amounts previously obtained for the subject.

23. A method according to claim 1, wherein the amount of lipid bound sialic acid determined in the blood plasma or serum sample is compared with a standard having a known concentration of lipid bound sialic acid which has been tested at the same time and by the same method as the sample with the effect that discrepancies in the test results attributable to variations in the techniques used in the test of the sample and the standard are eliminated.

* * * * *